(12) United States Patent
Lenke et al.

(10) Patent No.: US 8,368,893 B2
(45) Date of Patent: Feb. 5, 2013

(54) OPTICAL ASSEMBLY AND METHOD

(75) Inventors: James Hershell Lenke, York (GB); Kevin James Moon, York (GB); David Murray Goodall, York (GB)

(73) Assignee: Paraytec Limited (GB)

( * ) Notice: Subject to any disclaimer, the term of this patent is extended or adjusted under 35 U.S.C. 154(b) by 387 days.

(21) Appl. No.: 12/628,963

(22) Filed: Dec. 1, 2009

(65) Prior Publication Data

US 2010/0225898 A1 Sep. 9, 2010

(30) Foreign Application Priority Data

Mar. 9, 2009 (GB) .................................. 0903992.6

(51) Int. Cl.
*G01N 21/00* (2006.01)

(52) U.S. Cl. ......... 356/436; 356/344; 356/244; 356/246

(58) Field of Classification Search .................. 356/436, 356/344, 244, 246
See application file for complete search history.

(56) References Cited

U.S. PATENT DOCUMENTS

| 5,061,361 | A | 10/1991 | Gordon |
| 6,995,844 | B2 * | 2/2006 | Hafeman et al. ............... 356/433 |
| 7,041,493 | B2 * | 5/2006 | Rao ............................. 435/288.1 |
| 7,262,847 | B2 | 8/2007 | Goodall et al. |
| 2005/0255600 | A1 * | 11/2005 | Padmanabhan et al. ......... 436/63 |

FOREIGN PATENT DOCUMENTS

| EP | 0386925 A1 | 9/1990 |
| EP | 1530716 | 5/2005 |

OTHER PUBLICATIONS

Nelson and Shah, "Convective Diffusion Model for a Transport-Controlled Dissolution Rate Process", Journal of Pharmaceutical Sciences, vol. 64, No. 4, Apr. 1975, 610-614.
Nelson and Shah, "Evaluation of a Convective Diffusion Drug Dissolution Rate Model", Journal of Pharmaceutical Sciences, vol. 64, No. 9, Sep. 1975, 1518-1520.
Missel et al, "Reexamination of Convective Diffusion / Drug Dissolution in a Laminar Flow Channel: Accurate Prediction of Dissolution Rate", Pharmaceutical Research, vol. 21, No. 12, Dec. 2004, 2300-2306.
Yu et al, "Feasibility Studies of Utilizing Disk Intrinsic Dissolution Rate to Classify Drugs", International Journal of Pharmaceutics, 270, 2004, 221-227.
Swartz and Krull, "Developing and Validating Dissolution Procedures", LCGC North America, Chromatography Online, Feb. 1, 2008 http://chromatographyonline.findanalytichem.com/lcgc/article/articleDetail.jsp?id=494777.

(Continued)

*Primary Examiner* — Tarifur Chowdhury
*Assistant Examiner* — Isiaka Akanbi
(74) *Attorney, Agent, or Firm* — Fliesler Meyer LLP

(57) ABSTRACT

An optical apparatus and method comprising a light source, an array detector for area imaging and an optical cell assembly. The optical cell assembly comprises a chamber which is arranged to receive a sample of a material including an analyte, a fluid inlet and a fluid outlet coupled to the chamber. A fluid dissolution medium stream passes through the chamber such that the sample can dissolve into the dissolution medium. The chamber is in at least one light path created between the light source and the array detector. The array detector comprises a two dimensional array of detector locations arranged to provide an output signal indicative of the light absorbance of the analyte within the chamber such that the output of the array detector is indicative of the concentration profile of the analyte near the surface of the sample.

24 Claims, 10 Drawing Sheets

OTHER PUBLICATIONS

Berger et al, "Technical Note: Miniaturized Intrinsic Dissolution Rate (Mini-IDRTM) Measurement of Griseofulvin and Carbamazepine", Dissolution Technologies, Nov. 2007, 39-41.

"CE 7smart" system commercially available from Sotax AG of Switzerland.

Bruin et al, "Optimization and evaluation of the performance of arrangements for UV detection in high-resolution separations using fused-silica capillaries", Journal of Chromatography, 559 (1991) 163-181.

* cited by examiner

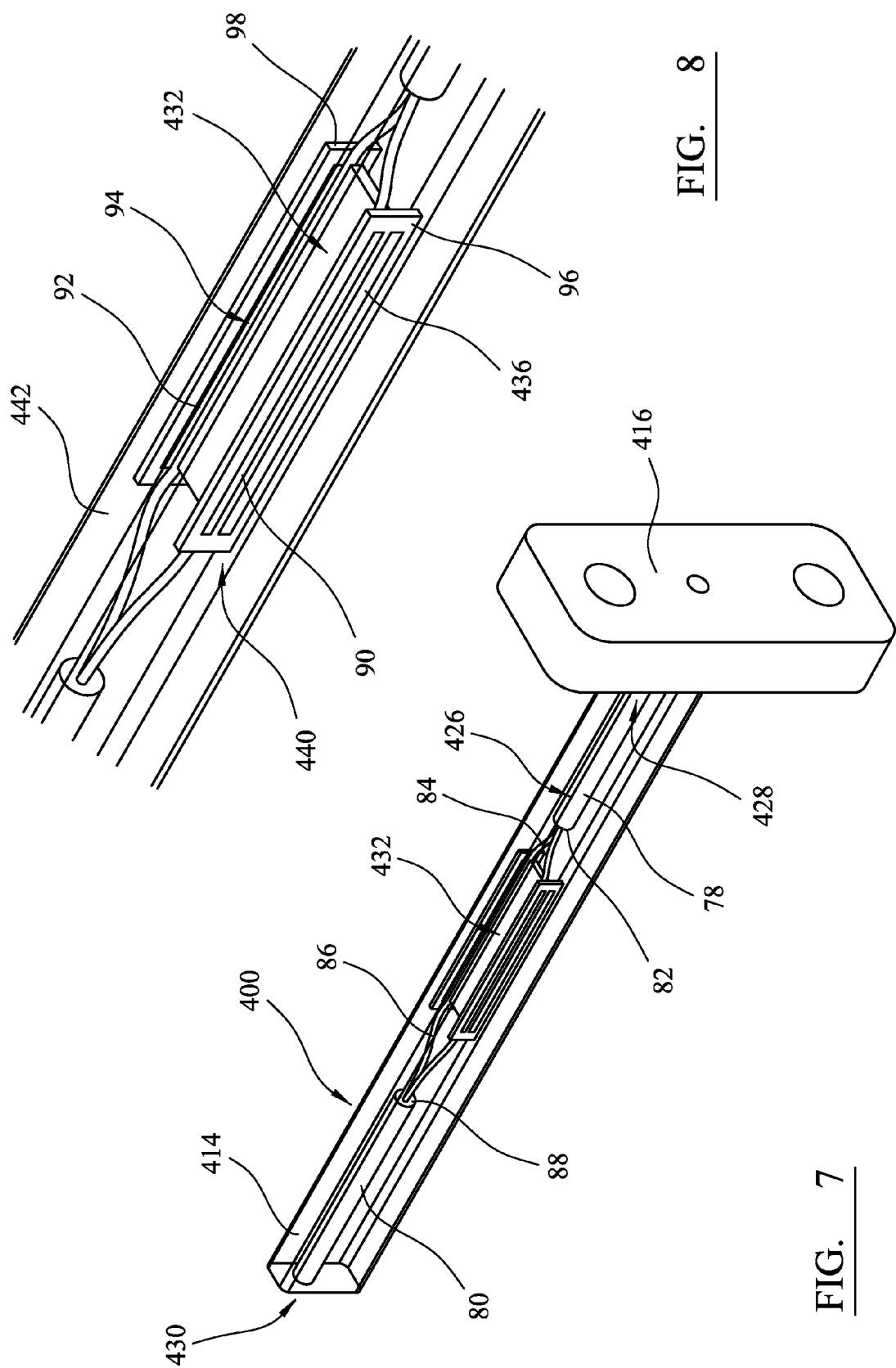

OPTICAL ASSEMBLY AND METHOD

The application claims priority under 35 U.S.C. 119 to U.K. Patent Application No. GB0903992.6, entitled "Optical Assembly and Method," inventors James Hershell Lenke et al., filed Mar. 9, 2009, which application is herein incorporated by reference.

FIELD OF THE INVENTION

The present invention relates to an optical assembly and method for imaging dissolution. An optical cell assembly for use in testing a sample of a material is disclosed together with a cartridge comprising such an optical cell assembly and an apparatus for testing a sample of a material, the apparatus incorporating the optical cell assembly. In particular, but not exclusively, the present invention relates to an optical apparatus for use in testing a sample of a material to image dissolution of the material into a fluid stream in which light from a light source is passed through a sample to be tested where the sample is dissolving into a fluid stream, the light passing in a direction transverse to a main axis of a fluid flow channel of the assembly.

BACKGROUND TO THE INVENTION

Ultra violet (UV) absorbance, fluorescence and mass spectrometry (MS) are key technologies used in separation science for analysing species (atoms, molecules, molecular fragments, ions, etc) in samples. One particular assembly which employs such techniques, with particular reference to UV and UV-visible (UV-vis) absorbance, is disclosed in U.S. Pat. No. 7,262,847 and European Patent No EP1530716 assigned to Paraytec Limited, the assignee of the present patent application, both of which are incorporated herein by reference for all purposes. U.S. Pat. No. 7,262,847 discloses an optical assembly comprising a light source, a number of sample vessels in the form of capillaries and a detector. The capillaries are positioned in a light path created between the source and the detector in a manner to enable transmission of light through the capillaries. The light source provides a beam of collimated light, and the detector has a plurality of detector locations. The capillaries each comprise a wall and a core of relative shape and dimensions adapted to contain a sample for detection, which is in a fluid stream flowing through the capillaries. The capillaries define spatially separated transmitted light paths including a first, wall path which enters and exits the walls only of each capillary and which is spatially separated from a second, core path which enters and exits the walls and additionally the core of the capillary. The spatially separated wall and core paths are coupled to individual detector locations on the detector.

The assembly and method disclosed in U.S. Pat. No. 7,262,847 has been found to be particularly effective in characterising species of interest in a fluid stream passing through the capillaries. However, fluid flowing along a conduit such as a capillary is subject to friction and thus shear both between walls of the conduit and the fluid, and indeed between layers within the fluid itself. Taylor dispersion effects result, in which a shear flow increases the effective diffusivity of a species in the fluid stream. In basic terms, the shear effects act to "smear" the concentration distribution in the direction of fluid flow, thereby enhancing a rate at which the species in question spreads out in that direction. For a given linear flow rate, this effect becomes more pronounced the greater the internal diameter of the tubing or capillaries such as those disclosed in U.S. Pat. No. 7,262,847 and, whilst this can have certain advantages in terms of characterising the species and determining other physical properties, in certain circumstances it may be desired to reduce the Taylor dispersion effects.

Small bore capillaries provide relatively small transverse path lengths for the light passing there through, and thus through small light path lengths through the sample contained within the capillaries. A method and apparatus for increasing detector sensitivity in a capillary zone electrophoresis detector is disclosed in U.S. Pat. No. 5,061,361 assigned to Hewlett-Packard Company and incorporated herein by reference for all purposes. The apparatus disclosed in U.S. Pat. No. 5,061,361 comprises a narrow bore capillary comprising a cell having a greatest diameter which is slightly larger than that of a remainder of the capillary, which provides an increased path length for light passing transversely through the cell. However, the ratio of the diameter of the cell relative to that of the capillary is relatively small, dictated by factors including manufacturing constraints, and thus only provides a relatively small increase in the path length.

It will be understood that the above described apparatus and methods have particular utility in analysing species in a fluid stream passing along a length of a capillary, which fluid has been prepared including a species to be analysed. However, these techniques are not easily applied, for example, to quantitative investigation of the dissolution of a material into a fluid stream at source. In particular, the apparatus disclosed in U.S. Pat. No. 5,061,361 cannot be applied to quantitative investigation of the dissolution of a material into a fluid stream at source.

One of the major challenges for formulation scientists when designing a tablet is ensuring that the active ingredient is released at the desired rate. The ability to visualize events at the tablet surface in real time can give valuable information about this process.

Pharmacoepial dissolution methods are the routine test of in-vitro product performance. Essentially, the drug sample in its deliverable form (e.g. a solid tablet or capsule) is placed in a solvent bath (usually an aqueous solution, the dissolution medium), which is mechanically stirred and kept at a controlled temperature. The solution is sampled to record the concentration of drug in the dissolution medium over time. The most widely accepted test, called the United States Pharmacopeia (USP) dissolution test, is based on this method. While product consistency can be measured, this provides little detailed information about the method of dissolution. Drug product dissolution is complex and involves several fundamental processes such as hydration, disintegration, erosion and particle de-agglomeration, as well as dissolution of the drug substance itself. Thus, where the prior art talks about "drug product dissolution", in reality what is referred to, imaged or attempted to be measured is in fact a combination of several processes.

Approaches currently used to assess drug product dissolution using imaging techniques include nuclear magnetic resonance imaging, Fourier transform infrared spectroscopy imaging and optical imaging using visible light. Specifically, it is known to use optical imaging using visible light to look directly at the surface of a solid sample to measure the rate at which the sample is dissolved. However, this technique cannot be applied to image the active dissolution of the sample into a fluid stream. Furthermore, most active ingredients in pharmaceuticals absorb in the UV spectrum rather than the visible region and so optical imaging using visible light is frequently ineffective.

It is known to seek to obtain the Intrinsic Dissolution Rate (IDR) of a sample through the measurement of dissolution of the sample into a fluid flow over a surface of the sample. The measurement of the IDR in this way is described in: Nelson & Shah, "Convective Diffusion Model for a Transport-Controlled Dissolution Rate Process", Journal of Pharmaceutical Sciences, Vol. 64, No. 4, April 1975, 610-614; Nelson & Shah, "Evaluation of a Convective Diffusion Drug Dissolution Rate Model", Journal of Pharmaceutical Sciences, Vol. 64, No. 9, September 1975, 1518-1520; Missel et al, "Reexamination of Convective Diffusion/Drug Dissolution in a Laminar Flow Channel: Accurate Prediction of Dissolution Rate", Pharmaceutical Research, Vol. 21, No. 12, December 2004, 2300-2306; and Yu et al, "Feasibility Studies of Utilizing Disk Intrinsic Dissolution Rate to Classify Drugs", International Journal of Pharmaceutics, 270, 2004, 221-227. However, the techniques described in all four papers assess the concentration downstream of the point of dissolution and therefore are ineffective for observing and measuring the process of drug product dissolution itself.

Similarly, Swartz and Krull, "Developing and Validating Dissolution Procedures", LCGC North America, Chromatography Online, Feb. 1, 2008 http://chromatographyonline.findanalytichem.com/lcgc/article/articleDetail.jsp?id=494777 provides an overview of conventional techniques for assessing the dissolution of a drug product. Again, however, there is no suggestion of observing and measuring the process of dissolution itself. Furthermore, the described techniques require large media volumes, for instance of the order of 500-1000 ml, which is disadvantageous.

Berger et al, "Technical Note: Miniaturized Intrinsic Dissolution Rate (Mini-IDR™) Measurement of Griseofulvin and Carbamazepine", Dissolution Technologies, November 2007, 39-41, teaches a miniaturised disk IDR system, which is essentially a miniaturised version of the approach taught in Yu et al. There is no teaching or suggestion of direct monitoring of the concentration profile of the active pharmaceutical ingredient near the surface, as is also the case for the above papers. Hence, this technique and the techniques described in the above papers are deficient as they are obliged to make assumptions regarding the concentration profile and fail to provide a technique of measuring this key parameter directly.

Similarly, the "CE 7smart" system commercially available from Sotax AG of Switzerland provides a conventional flow through dissolution system which requires a large media volume and fails to allow for measurement at or near the surface of the sample.

It is amongst the objects of at least one embodiment of the present invention to overcome disadvantages associated with the method and apparatus disclosed in U.S. Pat. No. 5,061,361, and to provide a new application of the method and apparatus disclosed in U.S. Pat. No. 7,262,847. In particular, it is an object of embodiments of the present invention to provide an improved optical apparatus and method for imaging the dissolution of a sample into a fluid stream.

SUMMARY OF THE INVENTION

According to a first aspect of the present invention there is provided an optical apparatus comprising: a light source; an array detector for area imaging; and an optical cell assembly comprising a chamber which is arranged to receive a sample of a material including an analyte, the optical cell assembly further comprising a fluid inlet and a fluid outlet coupled to the chamber and arranged to provide a fluid dissolution medium stream passing through the chamber such that the sample can dissolve into the dissolution medium; wherein the optical cell assembly is positioned such that the chamber is in at least one light path created between the light source and the array detector; and wherein the array detector comprises a two dimensional array of detector locations arranged to provide an output signal indicative of the light absorbance of the analyte within the chamber such that the output of the array detector is indicative of the concentration profile of the analyte near the surface of the sample.

Advantageously, the present invention allows active dissolution of a sample of a substance, for instance a drug product, into a fluid stream to be imaged at a micron scale. This can provide information on the dynamic concentration of the drug product close to the surface of the dissolving sample. The Intrinsic Dissolution Rate (IDR) can thus be calculated. The array detector can be a 2D active pixel area imaging array. This allows quantitative measurement of dissolution of an active ingredient from the surface of a pharmaceutical formulation, which is not achievable by any previously known technique. The detector, such as is described in U.S. Pat. No. 7,262,847, is chosen to provide over 3 orders of magnitude of linear dynamic range which assists in picking out wide difference in substance concentration to enable accurate profiling. Furthermore, the high spatial resolution of the detector can given sharp imaging down to 7 μm in a direction transverse to the surface to maximise information quality. Direct monitoring of the concentration profile of the active pharmaceutical ingredient near the surface can be performed, which is a key parameter for studying dissolution.

The plurality of detector locations may be arranged to provide a signal indicative of the two dimensional distribution of light absorbance of the dissolution medium and the analyte across at least part of the chamber.

The array detector may be arranged to receive light which passes through the chamber and light from the light source which does not pass though the chamber at spatially separated portions of the array detector such that light received directly from the light source may be used as a reference for light passing through the chamber.

The array detector may be arranged to receive light which passes through part of the chamber containing the dissolution medium and the analyte released into the dissolution medium and light from the light source which passes though part of the chamber containing only the dissolution medium at spatially separated portions of the array detector such that light received through only the dissolution medium may be used as a reference for light passing through the dissolution medium and the analyte.

The light source may emit at least one wavelength of light that is absorbed by the analyte comprised in the sample for detection, the absorbance of which is to be detected. The light source may be arranged to provide UV-visible light having a wavelength in the range 180 to 1200 nm.

The array detector may comprise a solid state sensing device, preferably a CMOS APS, a CCD or a CID.

The apparatus may further comprise a cartridge in which the optical cell assembly is received, the cartridge being arranged to mount the optical cell assembly relative to the light source and the array detector such that the chamber is in at least one light path created between the light source and the array detector, the cartridge comprising: a cartridge body having a pair of spaced, opposed arms; a passage extending through the arms and which passage is shaped to receive the optical cell assembly; wherein the arms define a space therebetween, which space extends in a direction transverse to the passage, and which space is positioned such that the optical cell assembly chamber is located within the space when the optical cell assembly is located within the passage, to thereby provide at least one path for light transmitted from the light source along the space and to the chamber for testing the sample in the chamber.

The optical cell assembly may comprise: a hollow outer cell portion; and an insert portion shaped to fit within the hollow outer cell portion; wherein the insert portion defines a fluid flow channel extending in a direction along a length of the insert portion and which comprises the fluid inlet, the fluid outlet and the chamber disposed between the inlet and the outlet, the chamber adapted to receive the sample and having a maximum width dimension in a direction transverse to a main axis of the fluid flow channel which is greater than a corresponding width of the inlet; and wherein the outer cell portion and the insert portion are arranged such that, when the insert portion is fitted within the outer cell portion, light from the light source can pass through the chamber in a direction along the width dimension of the chamber.

The chamber may have a maximum cross-sectional area in a plane transverse to a plane in which the fluid flow channel is disposed greater than a corresponding cross-sectional area of the inlet, and optionally also a corresponding cross-sectional area of the outlet.

The insert portion may comprise opposed lateral windows which open on to the chamber, the windows provided on respective side surfaces of the insert portion, the windows being closed when the insert portion is fitted within the outer cell portion.

The chamber may be at least partially bound by one or more walls defined by the insert portion, which wall or walls extend between the inlet and the outlet and are shaped to define a smooth transition from the inlet towards a region of the chamber of maximum width dimension and a smooth transition from the region of the chamber of the maximum width dimension towards the outlet.

The walls may be arcuate and shaped such that the chamber is generally parabolic in longitudinal cross-section in regions adjacent to the inlet and the outlet.

The chamber may comprise a receiving area for receiving a material, and a dissolution area.

The sample receiving area may be spaced from a side wall or walls of the insert portion, so as to define a gap or gaps between the side wall or walls and the sample receiving area.

The insert portion may comprise a main insert portion element defining the dissolution area, and a sample holder element defining the sample receiving area.

The sample receiving area may be a secondary chamber defined by the sample holder element.

The sample holder element may be adapted to be received within a recess in the main insert portion element.

The insert portion may define a charging channel for charging material into the chamber, and which charging channel is separate from the part of the fluid flow channel defining the inlet.

According to a second aspect of the present invention there is provided a detection method for measuring a concentration profile of an analyte near the surface of a sample, the method comprising: illuminating a chamber of an optical cell assembly with a light source, the chamber containing a sample of a material including an analyte, the optical cell assembly further comprising a fluid inlet and a fluid outlet coupled to the chamber; supplying a dissolution medium to the fluid inlet under pressure such that a fluid dissolution medium stream passes over the sample such that the sample can dissolve into the dissolution medium; detecting light from the light source passing through the chamber at an array detector, the array detector comprising a two dimensional array of detector locations; and generating at each detector location in the array detector a signal indicative of the light absorbance of the analyte at corresponding locations within the chamber along the light path from source to detector such that the output of the array detector is indicative of the concentration profile of the analyte near the surface of the sample.

The detection method may further comprise generating at the array detector a signal indicative of the two dimensional distribution of light absorbance of the dissolution medium and the analyte across the detection window.

The output of the array detector may be indicative of the concentration profile of the analyte downstream from the surface of the sample.

A first output of the array detector may be indicative of the flow profile of the dissolution medium downstream of the surface of the sample and a second output of the array detector may be indicative of the concentration profile of the analyte downstream of the surface of the sample. The method may further comprise determining the intrinsic dissolution rate of the sample from the flow profile of the dissolution medium downstream of the sample and the concentration profile of the analyte downstream of the surface of the sample.

The optical apparatus of the present invention may utilise an optical cell assembly arranged to introduce the sample to dissolve into the flow stream. The optical cell assembly may comprise a hollow outer cell portion; and an insert portion shaped to fit within the hollow outer cell portion; wherein the insert portion defines a fluid flow channel extending in a direction along a length of the insert portion and which comprises an inlet, an outlet and a chamber disposed between the inlet and the outlet, the chamber adapted to receive a sample to be tested and having a maximum width dimension in a direction transverse to a main axis of the fluid flow channel which is greater than a corresponding width of the inlet; and wherein the outer cell portion and the insert portion are arranged such that, when the insert portion is fitted within the outer cell portion, light from a light source can pass through the chamber in a direction along the width dimension of the chamber to test the sample in the chamber.

Providing an optical cell assembly for use in testing a sample of a material including an insert portion defining a fluid flow channel having such a chamber offers advantages over prior assemblies. These include that, by providing the fluid flow channel within the insert portion, the chamber can be provided with a much greater width dimension when compared, for example, to the cell disclosed in U.S. Pat. No. 5,061,361, the width of the chamber being dictated by the dimensions of the insert portion and not by manufacturing constraints relating to capillaries. Thus a much greater path length for light passing through the chamber can be provided than in prior apparatus such as that disclosed in U.S. Pat. No. 5,061,361.

Additionally, providing an optical cell assembly including a hollow outer cell portion, and an insert portion shaped to fit within the outer cell portion and which defines the chamber, facilitates charging of the chamber with any desired sample material to be tested. Furthermore, the present invention may permit repeated reuse, as the insert portion may be separable from the outer cell portion, facilitating cleaning and recharging of the chamber with a fresh sample of material to be tested.

The insert portion may be adapted to be releasably fitted within/separable from the outer cell portion, and may be arranged to be a sliding fit within the outer cell portion. The insert and outer cell portions may comprise elongate bodies.

The chamber may have a maximum width dimension, which is greater than corresponding widths of both the inlet and the outlet of the fluid flow channel. This may facilitate optimisation of fluid flow through the chamber, and in particular may facilitate promotion of laminar flow within and through the chamber. The chamber may have a maximum cross-sectional area (in a plane transverse to a plane in which the fluid flow channel is disposed) greater than a corresponding cross-sectional area of the inlet, and optionally also a corresponding cross-sectional area of the outlet.

The chamber may be adapted to receive a wide range of different types of material, and thus the optical cell assembly may be for use in testing samples of a wide range of different types of materials. These may include solids, liquids and/or multi-phase mixtures thereof, including two-phase materials optionally separated by a membrane or the like. Solids materials may, for example: be in pressed tablet form and may comprise one or more granular materials; may be in granular or powdered form; and/or may be a gel or mixture of gels. Solids tablets might comprise chemical or pharmaceutical products, optionally held in matrix of a different material such as a polymer. Liquids materials might be selected to be immiscible with a fluid flowing through the fluid flow channel or may be soluble. It will be understood that the embodiments of an optical cell assembly described above are particularly advantageous for use within the larger optical assembly of the present invention for analysing dissolution of a material into a fluid stream flowing along the fluid flow channel, the dissolution occurring within the chamber itself and for analysing the constituents of a material prepared externally of the chamber and passed along the fluid flow channel into the chamber.

The chamber defined by the insert portion may be open, and may be closed and optionally sealed when the insert portion is fitted within the outer cell portion. This may be achieved by appropriate dimensioning of the insert portion and the outer cell portion, and/or by providing an at least one seal or sealing element. The insert portion may comprise opposed lateral windows or apertures which open on to the chamber, the windows provided on respective side surfaces of the insert portion or spaced, for example, 180° apart around a circumference or perimeter of the insert portion (where the insert portion is circular, oval or elliptical in cross-section). The windows may have a major dimension extending in a direction along the length of the insert portion. The windows may be closed when the insert portion is fitted within the outer cell portion. The insert portion may comprise a frame or the like around or in each window, which frame may be integral or provided as a separate component, and which may stand proud of the respective wall. The frame may define a plurality of light paths through the chamber and may define: at least one reference flow path for the passage of light through a referencing fluid material optionally contained within the chamber; and at least one sample testing light flow path. The or each sealing element may seal the insert portion relative to the outer cell portion to restrict fluid egress from the chamber. The assembly may comprise at least two sealing elements, and may comprise one for each of first and second ends of the insert portion and the outer cell portion. Where the insert portion comprises windows and corresponding frames, the frames may serve for sealing the insert portion relative to the outer cell portion.

The chamber may be at least partially bound by one or more walls defined by the insert portion, which wall or walls may extend between the inlet and the outlet. The wall or walls may be shaped to define a smooth transition from the inlet towards a region of the chamber of maximum width dimension and/or of a maximum cross-sectional area. This may promote laminar flow from the inlet into the chamber. The wall or walls may be shaped to define a smooth transition from the region of the chamber of the maximum width dimension and/or maximum cross-sectional area towards the outlet, to similarly promote laminar flow out of the chamber. The wall, or one or more of the walls, may be arcuate, and may be shaped such that the chamber is generally parabolic in longitudinal cross-section in a region adjacent to the inlet, and optionally adjacent to the outlet, such that the chamber is generally elliptical in longitudinal cross-section. Said regions may alternatively be arcuate with a substantially constant radius of curvature, or at least part of the wall or walls may be inclined relative to the main axis of the fluid flow channel.

The chamber may comprise a receiving area for receiving a material, and a dissolution or mixing area. This may facilitate, for example, dissolution of a solids material into a fluid stream flowing along the flow channel into the dissolution area, and subsequent analysis of the resulting solution (which forms the sample of material to be tested); and/or creation of a two-phase suspension of solids particles in the fluid flowing through the flow channel, and subsequent analysis of the resulting suspension (which forms the sample of material to be tested). The sample receiving area may be spaced from a side wall or walls/edge(s) of the insert portion, so as to define a gap or gaps between the side wall or walls and the sample receiving area. This may provide benefits including the flow stream liquid in this region providing a sheath for liquid transporting material emanating from the sample receiving area. In turn this may provide a narrowing of velocity spread in any pixel element, allowing use of good depth of field and thickness of sample interrogated.

The insert portion and the outer cell portion may be arranged such that the light from the light source passes through the dissolution or mixing area. Thus where, for example, a material is charged into the sample receiving area and dissolves into a fluid flowing through the flow channel, the light will pass through the resultant fluid solution.

The insert portion may comprise a unitary/one-piece body defining the chamber and thus both the sample receiving area and the dissolution or mixing area. Alternatively, the insert portion may comprise a main insert portion element defining the dissolution or mixing area, and a sample holder element defining the sample receiving area. The sample receiving area may be a secondary chamber defined by the sample holder element, or a sub-chamber. The sample holder element may be adapted to be received within a recess or the like in the main insert portion element and may be received in a sliding fit. Advantageously, this facilitates charging/recharging of a material into the chamber, in particular into the sample receiving area. This may be achieved by separating the insert portion from the outer cell portion; separating the sample holder element from the main insert portion element; charging/recharging a material into the receiving area; refitting the sample holder element within the main insert portion element; and then refitting the insert portion within the outer cell portion.

The insert portion may define a charging channel for charging the sample into the chamber, and which charging channel may be separate from the part of the fluid flow channel defining the inlet. The charging channel may particularly serve for charging a fluid into the chamber, but may equally serve for charging solids or other materials into the chamber.

The chamber may be quadrilateral-shaped in cross-section and in particular may be rectangular or square. This may provide advantages in terms of providing a constant light path length throughout the chamber. Alternatively, the chamber may be generally circular, elliptical, oval or other suitable shape in cross-sections. Portions of the chamber may have different shapes in cross-section.

The assembly may comprise end caps for securing the insert portion relative to the outer cell portion and thus for restricting relative movement between the portions. The end caps may each comprise apertures for fluid communication with the fluid flow channel of the insert portion and thus for flow of fluid into, along and out of the flow channel. The assembly may be adapted to be coupled to a tube or capillary or capillaries for directing fluid into the fluid flow channel.

There is further provided a cartridge for an optical cell assembly as described, for loading the optical cell assembly into an optical assembly according to an embodiment of the present invention. The cartridge may comprise a cartridge body having a pair of spaced, opposed arms; a passage extending through the arms and which passage is shaped to receive the hollow outer cell portion of the optical cell assembly; wherein the arms define a space there between, which space extends in a direction transverse to the passage, and which space is positioned such that the chamber defined by the insert portion is located within the space when the insert portion is fitted within the outer cell portion and the outer cell portion is located within the passage, to thereby provide at least one path for light transmitted from a light source along the space and to the chamber for testing the sample in the chamber.

The optical cell assembly may comprise a hollow outer cell portion; and an insert portion shaped to fit within the hollow outer cell portion; wherein the insert portion defines a fluid flow channel extending in a direction along a length of the insert portion and which comprises an inlet, an outlet and a chamber disposed between the inlet and the outlet, the chamber adapted to receive a sample to be tested; and wherein the outer cell portion and the insert portion are arranged such that, when the insert portion is fitted within the outer cell portion, light from a light source can pass through the chamber to test the sample in the chamber.

The chamber may have a maximum width dimension in a direction transverse to a main axis of the fluid flow channel which is greater than a corresponding width of the inlet, and the outer cell portion and the insert portion may be arranged such that, when the insert portion is fitted within the outer cell portion, light from the light source can pass through the chamber in a direction along the width dimension of the chamber.

BRIEF DESCRIPTION OF THE FIGURES

Embodiments of the present invention will now be described, by way of example only, with reference to the accompanying drawings, in which:

FIG. 7 is a perspective view of part of an optical cell assembly in accordance with a yet further alternative embodiment of the present invention;

FIG. 8 is an enlarged view of a portion of the optical cell assembly shown in FIG. 7;

DETAILED DESCRIPTION OF EMBODIMENTS OF THE INVENTION

Figure 9:
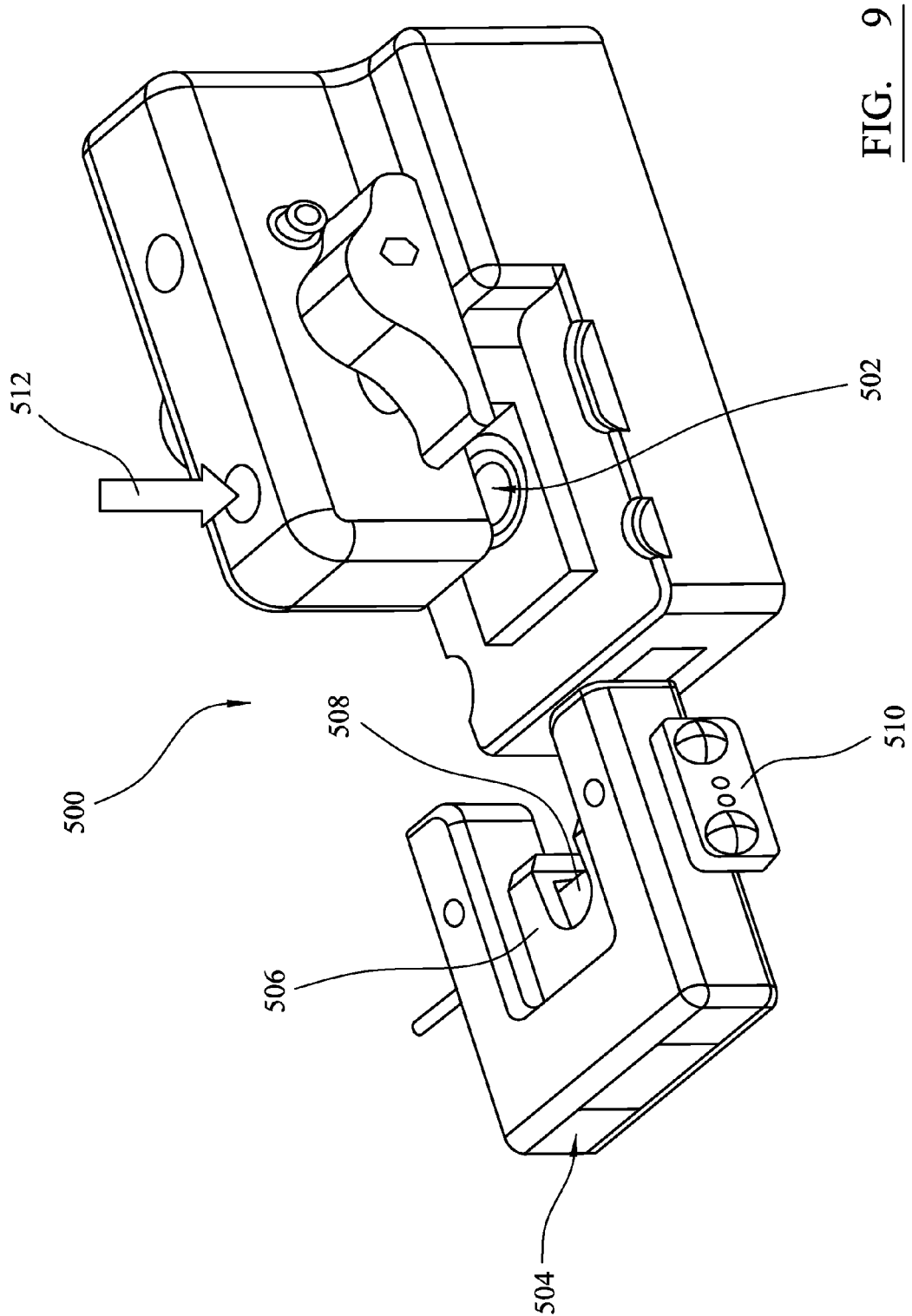
FIG. 9 is a perspective view of an optical apparatus for testing a sample of a material in accordance with an embodiment of the present invention including a cartridge according to FIG. 3 and an optical cell assembly according to FIG. 1.

FIGS. 1 to 8 illustrate optical cell assemblies and cartridges arranged to receive samples of materials to be tested, and are described first. The dissolution of the samples into a fluid flow is to be tested. FIG. 9 illustrates an optical assembly, including an optical cell assembly and a cartridge, for imaging the dissolution of the sample into the fluid flow.

Figure 1:
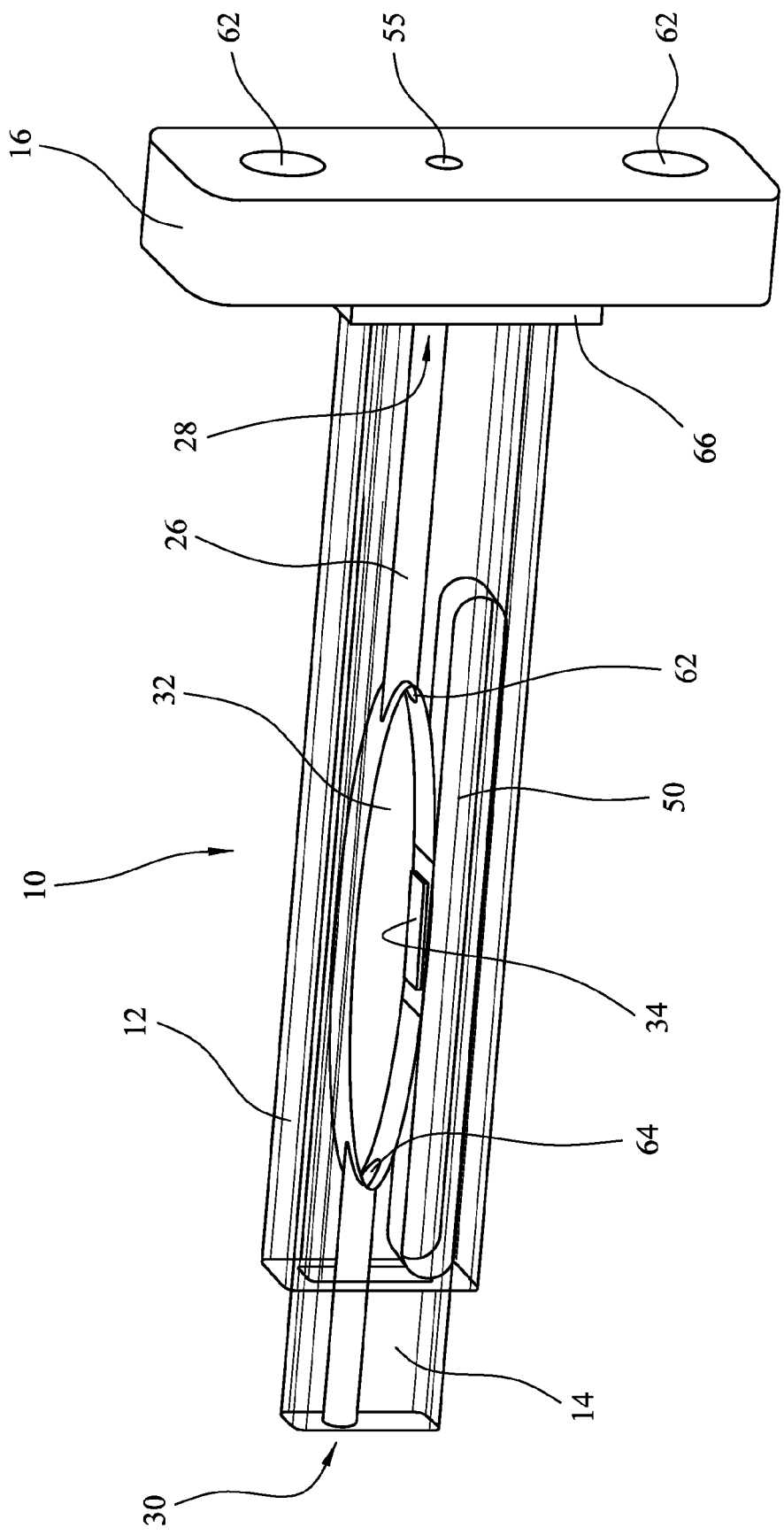
FIG. 1 is a perspective view of part of an optical cell assembly for use in testing a sample of material in accordance with an embodiment of the present invention.
Figure 2:
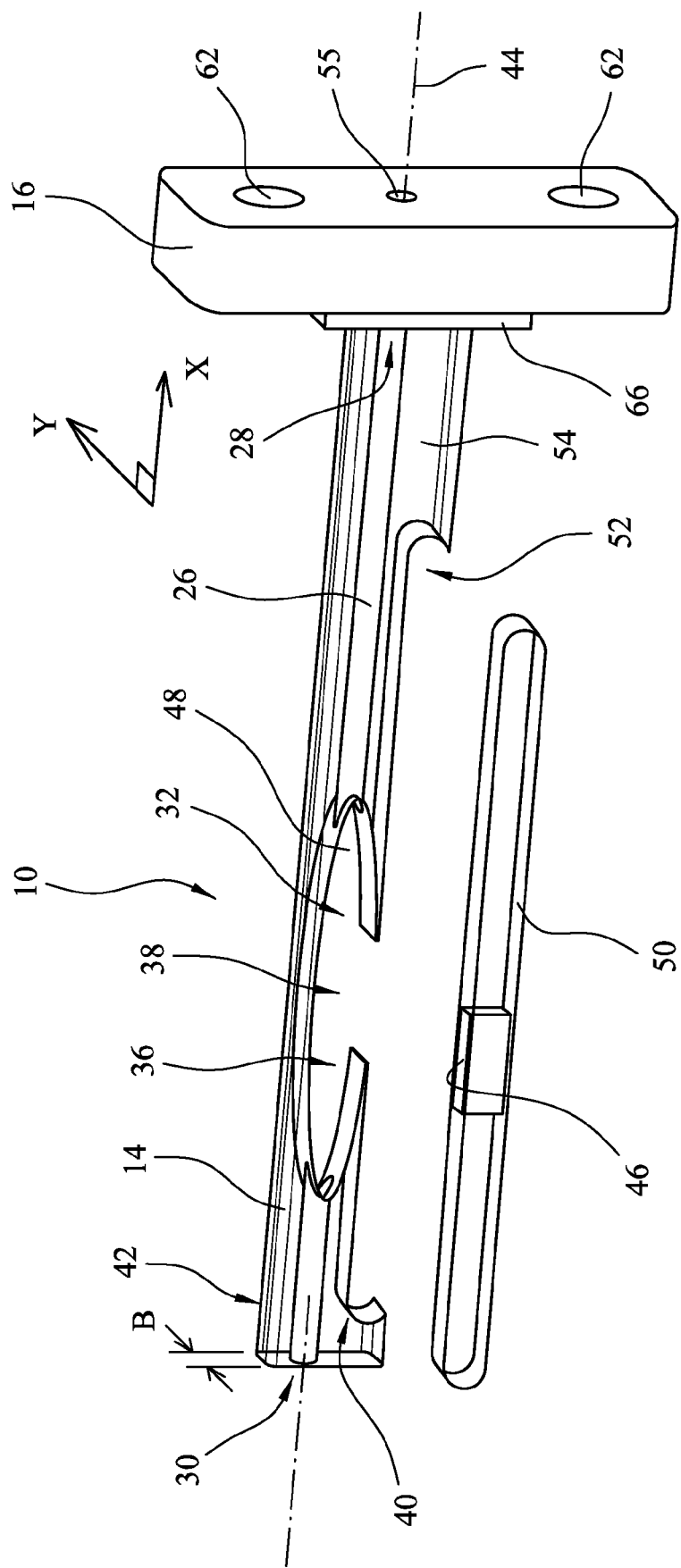
FIG. 2 is a view of the optical cell assembly of FIG. 1 with an outer cell portion of the assembly removed.

Turning firstly to FIG. 1, there is shown a perspective view of part of an optical cell assembly for use in testing a sample of material in accordance with an embodiment of the present invention, the optical cell assembly indicated generally by reference numeral 10. The assembly 10 generally comprises a hollow outer cell portion 12 and an insert portion 14 which is shaped to fit within the outer cell portion 12. In FIG. 1, part of the outer cell portion 12 has been removed to illustrate the relationship between the outer cell portion and the insert portion 14. Additionally and as will be described in more detail below, a single end cap 16 of the assembly 10 is shown in FIG. 1. A similar such end cap (not shown) is provided on an opposite end of the assembly 10, but has been removed from FIG. 1 for illustration purposes. Reference is also made to FIG. 2, which is a view similar to FIG. 1 but with the outer cell portion 12 removed, and which more clearly illustrates the insert portion 14 of the assembly.

Figure 3:
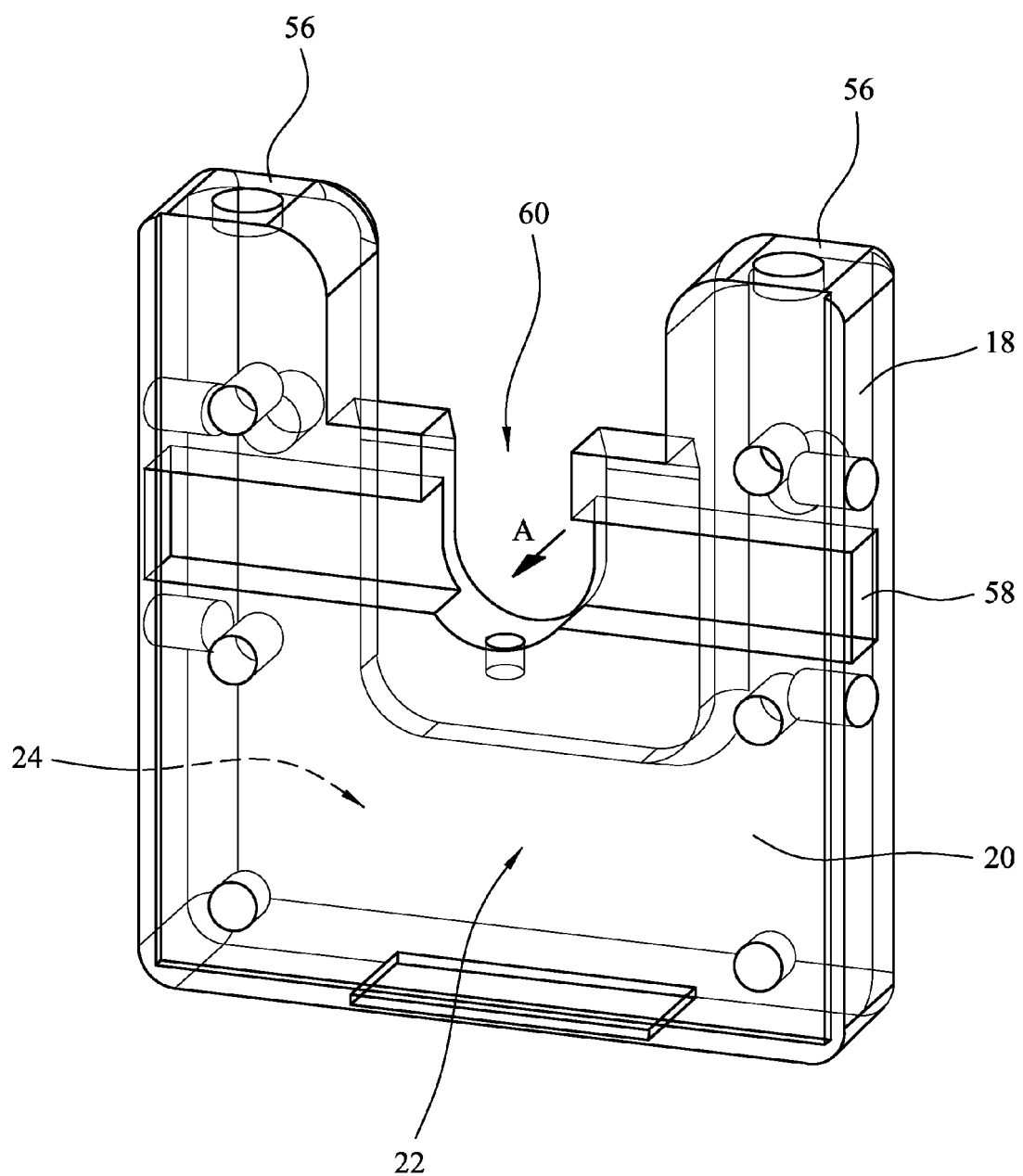
FIG. 3 is a perspective view of a cartridge for receiving the optical cell assembly of FIG. 1.

The optical cell assembly 10 is fitted into a cartridge 18, which is shown in the perspective view of FIG. 3, and which is drawn to a different scale from FIGS. 1 and 2. Hidden detail illustrating structural features of the cartridge 18 have been included in the drawing. The cartridge 18 is shaped to fit into optical apparatus for testing a sample of a material (not shown) of a type similar to that disclosed in U.S. Pat. No. 7,262,847 to the present applicant. Such apparatus is commercially available under the ActiPix Trade Mark and includes the ActiPix D100 and the ActiPix Nano-Sizing Systems. The cartridge 18 comprises a cartridge body 20 which is of a similar shape and function to the ActiPix sizing cartridge which is commercially available from the applicant, and which is for use with the ActiPix systems. In FIG. 3, a lower surface of the cartridge body 20 is designated with the reference numeral 22 whilst an upper surface is designated with the reference numeral 24. In use, light passes down through the cartridge 18 in the direction of the arrow A shown in FIG. 3, from a light source of the optical apparatus towards a detector of the apparatus, passing through the optical cell assembly 10, for analysing a sample of material in the cell assembly 10, as will be described below.

The structure of the assembly 10 will now be described in more detail. The outer cell portion 12 is, as noted above, hollow and shaped to receive the insert portion 14. The insert portion 14, best shown in FIG. 2, defines a fluid flow channel 26 which extends in a direction along a length of the insert portion 14, and which comprises an inlet 28, an outlet 30 and a chamber 32 disposed between the inlet and the outlet. The chamber 32 is adapted to receive a sample of a material to be tested. In the illustrated embodiment, a material 34 is located in a position where it is exposed to the fluid flowing along the flow channel 26 and through the chamber 32. The material 34 may be any one of a wide range of types of materials, and may be a solid, a liquid, or a two-phase material optionally separated by a membrane, amongst other things. In FIG. 1 however, the material 34 is a solid and comprises a pressed pellet or tablet of granular material comprising a chemical or pharmaceutical product which may be in a polymer matrix. The tablet 34 may comprise a substance which dissolves into the fluid flowing along the flow channel 26 to form a solution carrying species to be analysed using the optical apparatus; or the tablet 34 may break down on exposure to the fluid to form a two-phase sample material comprising solids particles in suspension with the fluid, to be analysed.

The chamber 32 extends through the insert portion 14, which includes a pair of opposed windows 36 and 38 in respective side walls 40 and 42 that open on to the chamber 32, as best shown in FIG. 2. The chamber 32 has a maximum width in a direction transverse to a main axis 44 of the fluid flow channel 26 (in an X-Y plane: FIG. 2) which is greater than a corresponding width of the inlet 38 and also of the outlet 30. It will be appreciated that the maximum width of the chamber 32 is governed by and equal to the width of the insert portion 14, as shown at B in FIG. 2.

The insert portion 14 is dimensioned to be a sliding fit within the outer cell portion 12, and the outer cell and insert portions are arranged such that, when the insert portion is fitted within the outer cell portion, light from the light source of the optical apparatus can pass through the chamber 32 in a direction along the width dimension of the chamber, to test the sample material in the chamber. In FIG. 1, the sample to be tested is the fluid solution or two-phase, solids-containing liquid contained within the chamber 32 resulting from exposure of the tablet 34 to the fluid passing along the flow channel 26.

Providing the chamber 32 in the insert portion 14 offers numerous advantages over prior assemblies. A key benefit is that this allows imaging of an area encompassing both the surface of the fluid and the flow stream, in two spatial dimensions in a plane normal to the light path direction. Additionally, providing the optical cell assembly with the insert portion 14 located within the outer cell portion 12, and the insert portion arranged in a sliding fit, facilitates charging of the tablet 34 into the chamber 32 of the insert portion 14, and indeed separation and recharging in a further testing procedure. Furthermore, the chamber 32 provides a relatively long optical path length for the light passing through the sample in the chamber 32, thereby providing good analytical sensitivity.

In the embodiment shown in FIGS. 1 and 2, the chamber 32 comprises a sample receiving area 46 for receiving the tablet 34, and a dissolution or mixing area 48. The sample receiving area 46 is in fact provided in a sample holder element 50 which is a sliding fit within a recess 52 in a main insert portion element 54. Thus and as shown in FIG. 1, fluid flowing along the flow channel 26 from the inlet 28 to the outlet 30 will enter the chamber 32 whereupon it is exposed to the sample 34. Solids material from the sample 34 dissolves into (or mixes with) the fluid in the chamber 32 and is carried along towards the outlet 30. Physical properties of this sample can then be determined from analysing the light passing through the chamber 32 from the light source to the detector, following the teachings of U.S. Pat. No. 7,262,847.

The sample receiving area 46 is spaced from the side wall 40, 42 of the insert portion 14, so as to define gaps between the side wall and the sample receiving area. This provides benefits including the flow stream liquid in this region providing a sheath for liquid transporting material emanating from the sample receiving area 46. In turn this may provide a narrowing of velocity spread in any pixel element, allowing use of good depth of field and thickness of sample interrogated.

The chamber 32 is generally elliptical in longitudinal cross-section, providing a smooth transition inwardly from inlet and outlet ends 62 and 64 (FIG. 1) of the chamber towards the centre of the chamber, which is of the greatest cross-sectional area. This provides good flow characteristics for fluid flowing along the channel 26 from the inlet 28 and into the chamber 32, and indeed from the chamber 32 along the channel towards the outlet 30, thereby promoting laminar flow. This in turn provides for good dissolution characteristics of the sample 34 into the fluid flowing along the channel 26. Tubing or capillaries (not shown in FIGS. 1 and 2) are coupled to the end caps 16 for the supply of fluid into and out of the cell assembly 100 through flow ports 55 in the end caps. Typically, the inlet and outlet will have diameters of around 400 microns, and the linear flow rate of fluid along the flow channel 26 will be in the range of 0.01 to 10 mm/s.

The invention has a particular utility in area imaging, and facilitates imaging on a micron scale, which is appropriate as the key profile of surface dissolution of a material in the receiving area 46 into a stream flowing parallel to the surface (along the fluid flow channel 26) is revealed at this scale of distance from the surface of the material in the area 46. Also, UV imaging is considered to be particularly helpful, since the UV region of the optical spectrum is where (for example) active pharmaceutical ingredients tend to absorb light.

Returning now to the cartridge 18 shown in FIG. 3, the general structure of the cartridge is as follows. The cartridge comprises main body 20, which includes a pair of spaced opposed arms 56. A passage 58 extends through the arms 56 and is shaped to receive the hollow outer cell portion 12 of the cell assembly 10. A space 60 is defined between the arms 56 and extends in a direction transverse to the passage 58 between the upper and lower surfaces 24, 22 of the cartridge body 20. In use, the outer cell portion 12 is located in the passage 58, and the insert portion 14 with the tablet 34 charged into the receiving area 46 of the sample holder element 50 is inserted into the outer cell portion 12, and slid along until the end of the insert portion 14 ends lie flush with external surfaces of the outer cell portion 12 and with the cartridge body 20. The chamber 32 is then located centrally within the space 60, so that light passing from the light source to the detector (in the direction of the arrow A) passes through the chamber 32, as described above.

The outer cell portion 12 will typically be of a fused silica (quartz) material and the insert portion 14 is typically microfabricated in a rapid prototyping process such as a stereolithography (SLA) process. Use of a micro-fabrication process facilitates formation of the complex internal structure of the insert portion 14.

Figure 4:
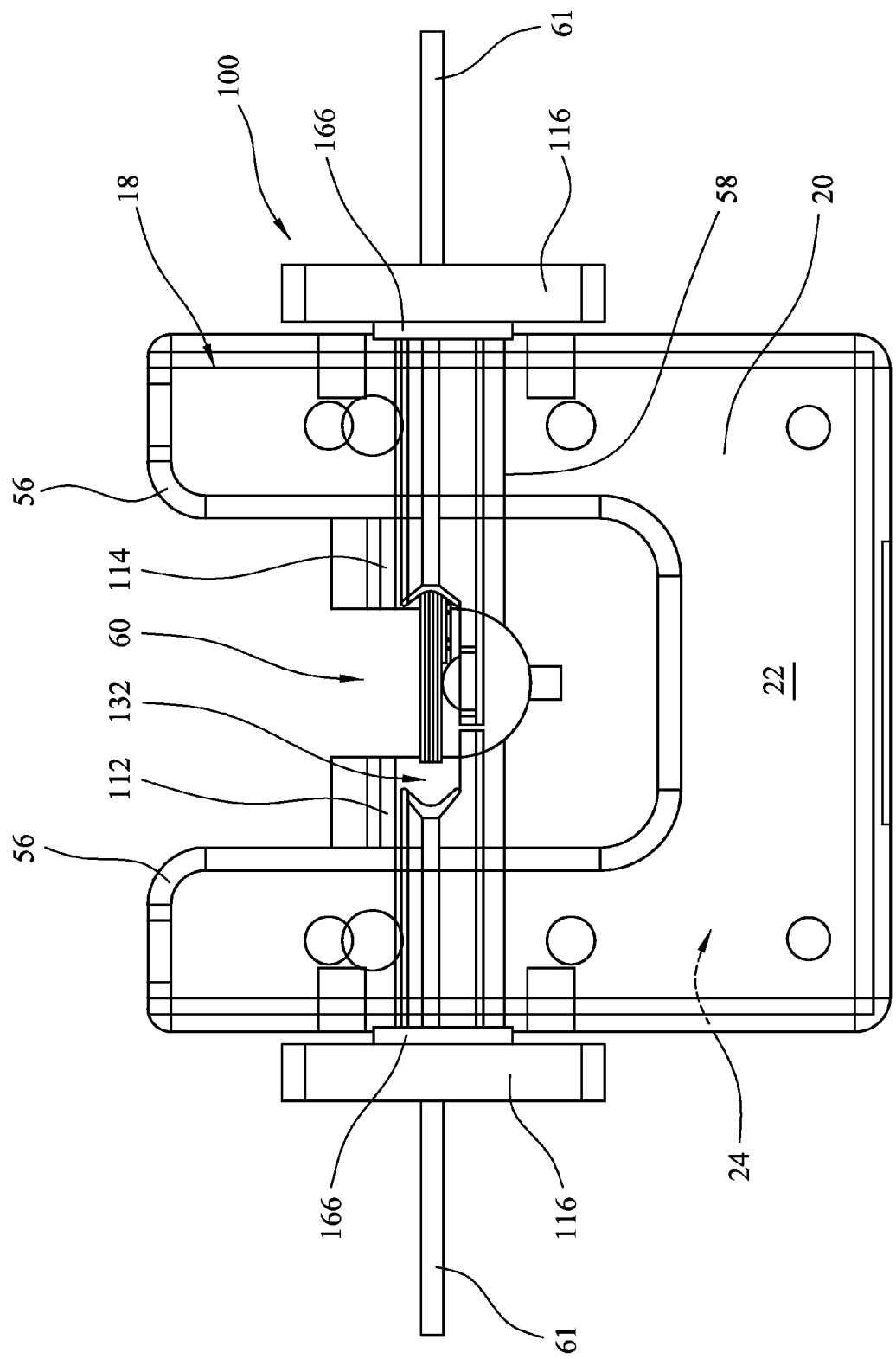
FIG. 4 is a plan view of the cartridge of FIG. 3, with an optical cell assembly in accordance with an alternative embodiment of the invention located therein.

The outer cell portion 12 and insert portion 14 are dimensioned to be a close sliding fit, to reduce the likelihood of fluid egress from the chamber 32 at the interface between the insert and outer cell portions. However, sealing assemblies in the form of elastomeric seals (one shown and given the reference numeral 66) are provided on each end cap 16. Thus when the cell assembly 10 is fitted within the cartridge body 20 as shown in FIG. 4 for the cell assembly 100, the seals 66 prevent any fluid egress from the chamber 32. The outer cell portion 12 and the insert portion 14 are fixed within the cartridge body 20 by the end caps 16, which are secured using screws (not shown) that pass through bores 62 in the end caps. Tubes or capillaries (not shown) connect to the end caps for supplying fluid into the chamber 32.

Figure 3A:
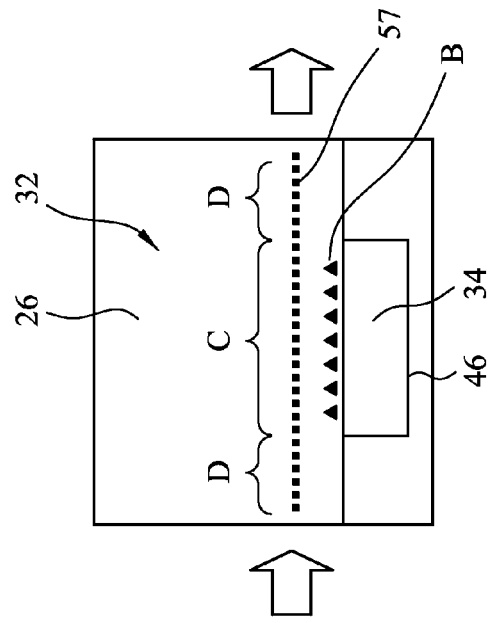
FIGS. 3A, 3B and 3C are schematic illustrations of the flow of fluid along a fluid flow channel of the assembly of FIG. 1.
Figure 3C:
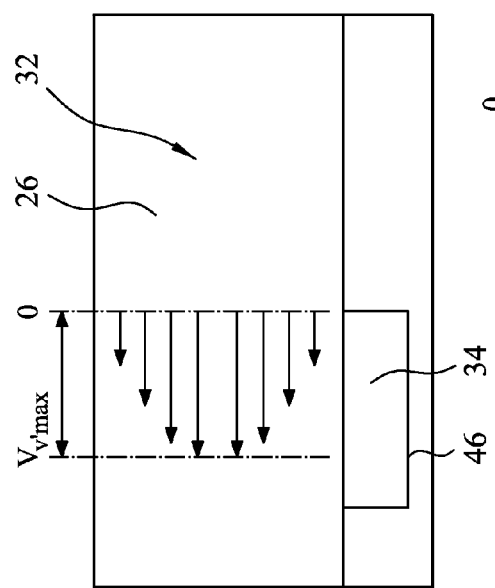
Figure 3B:
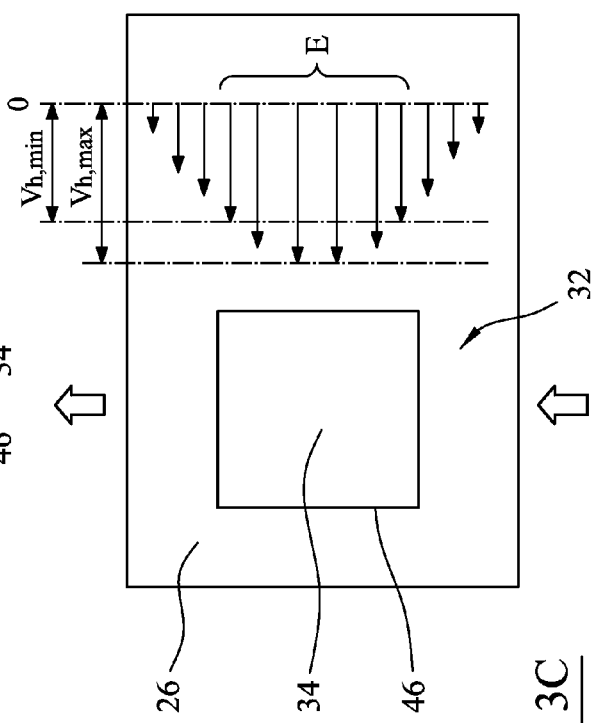

FIGS. 3A, 3B and 3C, schematically illustrate the flow of fluid along the flow channel 26, and the separation of material from the sample 34. Considering FIG. 3A, this is a view into the chamber 32 from the window 36 where a light beam enters, showing a well defined velocity profile in a vertical direction in the fluid stream in a plane away from the sample 34 surface. FIG. 3B, which is a view taken in the direction of fluid flow along the channel 26, shows separation of material from the sample 34 from the side windows 36 and 38 of the chamber 32, and illustrating benefits of this. A sample dissolving into the flow stream and diffusing up from the surface of the sample 34 is shown by the arrow heads B. Conversion of these into the sample moving in the flow stream is indicated by the portion C of a line 57. A sheath effect is provided by fluid in the flow stream between a region above the sample receiving area 46 and the walls (the portions D of the line 57), which ensures a narrow range of velocity vectors for dissolved sample advected in the flow stream direction. This in turn means absorbance of light at a fixed distance above the surface of the sample 34 is due to sample with a very small velocity spread (see also FIG. 3C). FIG. 3C is a view down onto the surface of the sample 34, showing a velocity profile in a horizontal plane of the flow stream. Separation from the side windows 36 and 38 of the chamber 32 means flow velocity vectors in the horizontal plane lie in a narrow range from $v_{h,min}$ to $v_{h,max}$ (vectors indicated by E in the figure). This provides benefits including low Taylor dispersion in the image of horizontal plane at any height above the surface for sample dissolving in the flow stream.

FIG. 4 illustrates an optical cell assembly 100 in accordance with an alternative embodiment of the present invention, and which is of similar construction to the cell assembly 10. Like components of the optical cell assembly 100 with the assembly 10 of FIGS. 1 and 2 share the same reference numerals, incremented by 100. The assembly 10 is shown in the figure located and fixed within the cartridge body 20 and end caps 116 are shown fixing the cell assembly 100 within the cartridge 18. It will be noted the assembly 100 is of similar construction to the cell assembly 10, save that a chamber 132 is of a different shape; part of a hollow outer cell portion 112 and insert portion 114 of the assembly 100 has been cut away in the figure, for illustration purposes. Capillaries 61 are shown in the figure and connect to the end caps 116, to supply fluid into the chamber 132.

Figure 5:
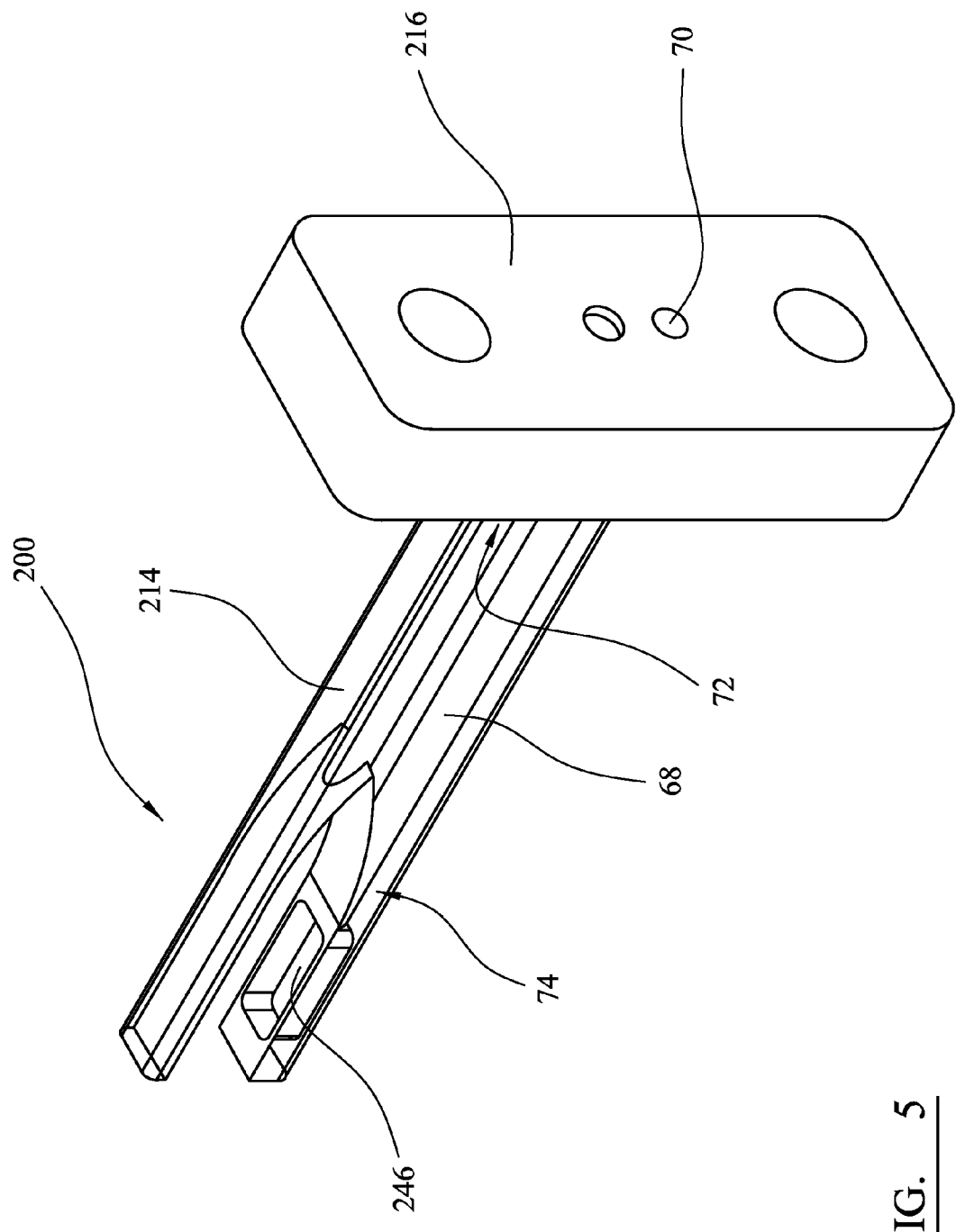
FIG. 5 is a perspective view of part of an optical assembly in accordance with a further embodiment of the present invention.

Turning now to FIG. 5, there is shown a perspective view of part of an optical assembly in accordance with a further embodiment of the present invention, the assembly indicated generally by reference numeral 200. Like components of the assembly 200 with the assembly 10 of FIGS. 1 and 2 share the same reference numerals, incremented by 200. FIG. 5 in fact shows only a part of an insert portion 214 and an end cap 216 of the assembly 200, the remainder of the insert portion 214 being cut-away, for illustration purposes. The assembly 200 includes an outer cell portion (not shown) similar to the outer cell portion 12 of the assembly 10, and is fitted into the cartridge 18 in a similar fashion.

The insert portion 214 differs from the portion 14 of the assembly 10 in that it includes a secondary, charging channel 68 for charging a material into a sample receiving area 246. The charging channel 68 is a hollow passage which communicates with the sample receiving area 246, and which is particularly suitable for charging a fluid into the area 246. However, it will be understood that other materials including solids may be charged into the receiving area 246 along the charging channel 68. The end cap 216 includes an inlet 70 which communicates with a corresponding inlet 72 of the charging channel 68 defined by the insert portion 214. An outlet or opening 74 of the charging channel 68 communicates with the receiving area 246 for charging the fluid into the area. The insert portion 214 also differs from the insert portion 14 of the assembly 10 in that it is a unitary body, and does not include a separate sample holder element. Typically, the sample receiving area will contain a membrane (not shown), which may be of a polymer material that is insoluble with the fluid flowing along the fluid flow channel 226. A fluid is charged into the area 246 beneath the membrane and diffusion of the fluid into the fluid flowing along the flow channel 226 is analysed.

Figure 6:
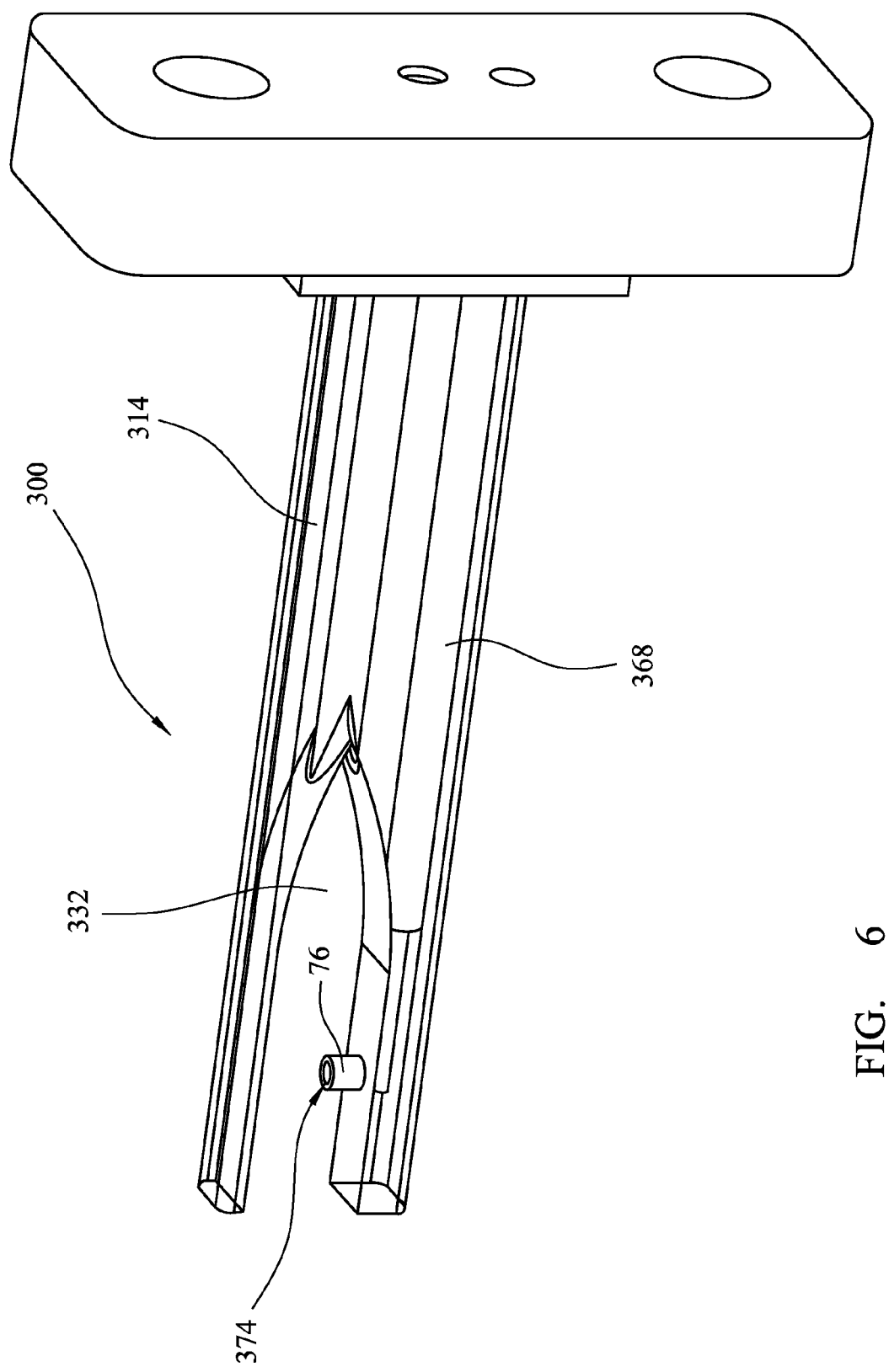
FIG. 6 is a perspective view of part of an optical cell assembly in accordance with a still further alternative embodiment of the present invention.

Turning now to FIG. 6, there is shown a perspective view of part of an optical cell assembly in accordance with a further alternative embodiment of the present invention, the assembly indicated generally by reference numeral 300. The assembly 300 is in fact of similar construction to the assembly 200 shown in FIG. 5. Like components of the assembly 300 with the assembly 10 of FIGS. 1 and 2 and with the assembly 200 of FIG. 6 share the same reference numerals, incremented by 300. As with FIG. 5, FIG. 6 shows part of an insert portion 314 of the assembly 300, which fits into a hollow outer cell portion (not shown) such as the portion 12 of the assembly 10. The insert portion 314 includes a charging channel 368 which includes an outlet 374 defined by a short tube 76 and which extends into a chamber 332. The charging channel 368 is particularly suited for charging a fluid into the chamber 332, which may occur prior to entry of fluid into the chamber along the flow channel 26; following entry of such fluid but with a static volume of the fluid in the chamber; or during the flow of fluid through the chamber 32 along the flow channel 26. The assembly 300 has a particular utility in observing diffusion or material transfer from the outlet 374 into the flow stream in chamber 332.

Turning now to FIG. 7, there is shown a perspective view of part of an optical cell assembly in accordance with a still further alternative embodiment of the present invention, the assembly indicated generally by reference numeral 400. Like components of the assembly 400 with the assembly 10 of FIGS. 1 and 2 share the same reference numerals, incremented by 400. Once again, only an insert portion 414 and end cap 416 of the assembly 400 is shown. However, the insert portion 414 is shown in full in the figure. It will be understood that the assembly 400 includes an outer cell portion (not shown) similar to the portion 12 of the assembly 10.

The insert portion 414 defines a fluid flow channel 426 having an inlet 428 and an outlet 430, the inlet 428 defined by an inlet channel portion 78 and the outlet by an outlet channel portion 80. At an end 82 of the inlet channel portion 78, the channel 426 narrows to a smaller diameter and includes a transition portion 84 which provides a transition from the small cylindrical bore at 82 to a rectangular cross-section chamber 432. The channel 426 is narrowed so as to reduce parabolic flow effects which would otherwise exist within the fluid entering the flow channel. The transition portion 84 provides a smooth transition from the small bore end 82 of the inlet channel portion 78 to the rectangular cross-section chamber 432, thereby promoting laminar flow. A similar transition portion 86 provides a transition from the chamber 32 to an end 88 of the outlet channel portion 80, once again to promote laminar flow. The shape of the chamber and the disposition of the sample are such that Taylor dispersion effects are reduced when compared to prior assemblies. In particular, a benefit of this embodiment is that parabolic flow profile and Taylor dispersion is determined by the short dimension, thus in the direction of observation (the long dimension) the velocity profile is flat except at the input and output wall region. Indeed, generically, for all embodiments discussed, Taylor dispersion is reduced relative to theoretical circular cross section cells of equivalent cross sectional area.

The insert portion 414 includes two windows (one shown and given the reference numeral 436), best shown in the enlarged view of FIG. 8, which open on to the chamber 432, and provide paths for light passing from the light source to the detector through the chamber 432. Additionally however, further windows 90 and 92 are provided, which communicate with a separate, reference chamber 94. The windows 90 and 92 provide a path for light from the source to the detector through air or a liquid contained within the reference chamber 94, which provides a reference for the material in the chamber 432 which is to undergo testing. The windows 436, 90 and 92 in the insert 414 are all defined by frames 96 and 98 which stand proud of side walls 440 and 442 of the insert portion 414. These frames 96 and 98 not only define the windows, but also provide a seal with the outer cell portion when the insert portion 414 is located within the outer cell portion. This provides a primary barrier to the egress of fluid from both the chamber 432 and the reference chamber 94. The assembly 400 has a particular utility in analysing species in a fluid which is prepared externally of the assembly and directed into the chamber 432 along the flow channel 426.

In a variation on the assembly 400, a microcapillary film (not shown), such as that available from Lamina Dielectrics Ltd, may be utilised. These are typically rectangular in cross-section and comprise a number of discrete axially extending flow passages. The films can be formed into an annular ring and located within a carrier tube, and may be utilised in place of capillaries or tubes coupled to end caps of the assembly 400. This offers advantages in terms of reducing parabolic flow effects to provide a column of fluid entering the fluid flow passage 426. When using such tubes, the narrowing of the flow passage bore 426 and the transition portions 84 and 86 may be dispensed with. The basic topology of use of microcapillary film is to take a flexible, compressible thin plastic rectangular film with flow channels therein and to wrap one end round as a spiral, with one short edge at the centre and the other short edge at the circumference. This provides an essentially circular input to use as a round to line fluid flow converter to insert between the end of the tube and the viewing area of the cell, with all channels within the film having constant length flow paths.

Optical cell assemblies may form part of optical assemblies in accordance with embodiments of the present invention which comprise one or more features of one or more of the above described optical cell assemblies.

A reference chamber or area containing a fluid may be defined in one or more of the embodiments of FIGS. 1, 4, 5 and 6 to provide a reference for the sample being tested. The reference chamber or area may be isolated from fluid in the fluid flow channel, and may be defined within the chamber of the insert portion.

The chamber may have a maximum cross-sectional area (in a plane transverse to a plane in which the fluid flow channel is disposed) greater than a corresponding cross-sectional area of the inlet, and optionally also a corresponding cross-sectional area of the outlet.

The chamber may be adapted to receive a wide range of different types of material, and thus the optical cell assembly may be for use in testing samples of a wide range of different types of materials. These may include solids, liquids and/or multi-phase mixtures thereof, including two-phase materials optionally separated by a membrane or the like. Solids materials may, for example: be in pressed tablet form and may comprise one or more granular materials; may be in granular or powdered form; and/or may be a gel or mixture of gels. Solids tablets might comprise chemical or pharmaceutical products, optionally held in matrix of a different material such as a polymer. Liquids materials might be selected to be immiscible with a fluid flowing through the fluid flow channel or may be soluble. It will be understood that the present invention has a utility both in analysing dissolution of a material into a fluid stream flowing along the fluid flow channel, the dissolution occurring within the chamber itself; and in for analysing the constituents of a material prepared externally of the chamber and passed along the fluid flow channel into the chamber.

Where the insert portion comprise opposed lateral windows or apertures which open on to the chamber, the windows may be provided spaced, for example, 180° apart around a circumference or perimeter of the insert portion (where the insert portion is circular, oval or elliptical in cross-section).

The wall, or one or more of the walls, of the insert portion which define the chamber may be arcuate with a substantially constant radius of curvature, or at least part of the wall or walls may be inclined relative to the main axis of the fluid flow channel.

The chamber may be generally circular, elliptical, oval or other suitable shape in cross-sections (in a plane perpendicular to a plane containing the main axis of the fluid flow channel). Portions of the chamber may have different shapes in cross-section. A key issues may be a desire to have smooth profiles without discontinuities in the flow direction, to prevent turbulence.

In the above described embodiments of an optical cell assembly, the fluid flow channels each lie on a respective straight, main longitudinal axes. It will be understood that shape of channel may vary along a length of the insert portion, and may comprise a number of sections each lying on respective axes which are at non-parallel angles. In this event, the maximum width direction may be taken relative to a main axis of a section of the fluid flow channel containing/forming the chamber.

In the foregoing description the term optical cell assembly has generally been used. It will be understood that the assembly may be generally referred to also as an optical vessel or optical vessel assembly.

There will now be described an optical apparatus in accordance with an embodiment of the present invention, incorporating optical cell assemblies and cartridges according to the embodiments described above.

Theories covering the dissolution of chemical substances stress the importance of the concentration gradient between the solid/solution interface and the bulk solution. UV imaging at the micron scale, such as is facilitated by the optical assembly of U.S. Pat. No. 7,262,847 allow this concentration to be investigated.

Turning now to FIG. 9, this illustrates the optical apparatus 500. The optical assembly 500 of FIG. 9 contains a 9 mm by 7 mm area imaging sensor 502 according to U.S. Pat. No. 7,262,847. The area imaging sensor 502 is an active pixel sensor containing an array of 1.3 million individually addressable active pixels and provides high speed imaging with a spatial resolution down to 7 microns. The cartridge 504 is as described above in connection with FIG. 3 and the optical cell assembly 506 is as described above in connection with FIG. 1, although it will be appreciated that the alternative optical cell assemblies described above may be used according to the properties of the sample under test. A dissolution medium is pumped through the optical cell assembly chamber 508 through inlet 510. For instance, the dissolution medium may be driven by a syringe pump. The chamber 508 contains a plug of a solid drug substance (the sample), although it will be appreciated that using the alternative optical cell assemblies described above alternative forms of samples may be used.

The chamber 508 is arranged between the sensor 502 and the source of filtered UV light 512, which is in accordance with U.S. Pat. No. 7,262,847. Illumination is provided at a wavelength which is absorbed by the active ingredient within the sample, e.g. 254 nm, using a pulsed xenon lamp and 10 nm bandpass filter. The 2D spatial profile of the transmitted light intensity is captured for each snapshot, and data captured at an appropriate frame rate (currently with an upper limit of 5 Hz, though this may be increased in the future) using the active pixel sensor 502. Pixel intensities (that is, the intensity of the received light) can be directly converted to absorbance values. After selecting regions of interest, e.g. up to a few hundred microns from the surface of the sample, the image frames can be used to generate absorbance measurements for each 7×7 micron pixel as a function of time. For higher speed imaging, the pixels can be grouped into sets of effective pixels (e.g. of dimension 70×7 micron). Additionally, the image frames generated can then be exported to a software package for analysing image data to interrogate key events.

The resulting plume of dissolved drug substance is monitored using the sensor 502 with intensities processed as absorbance values as described within U.S. Pat. No. 7,262,847. The dissolution medium, typically chosen to simulate physiological conditions, is driven over the sample surface. The media may be readily changed by switching the pump source. Similarly, as described above, the sample within the optical cell assembly may be readily changed.

The UV or UV-vis images may be acquired at up to 5 times per second and processed to give absorbance profiles from sections of the total image. UV imaging using the optical assembly of FIG. 9 has been demonstrated to provide information on the dynamic concentration gradient close to the surface of dissolving drug substances. Direct dissolution of the sample into the medium can be observed, together with the release of particles of the active ingredient from the sample surface. Convective diffusion of the sample may also be measured by the same technique. The removal of released or dissolved particles by the flowing media can be measured. The latter process has been modeled, assuming dissolution from a planar tablet surface, development of a diffusion gradient at 90° to the surface, and flow parallel to the surface. Preliminary data for dissolution of a benzoic acid tablet show that simulations model the profiles of the real-time observations.

Dissolution can be measured as a function of distance off the surface of the sample. This allows the real time interaction of a sample with a dissolution medium of choice to be measured. Downstream absorbance and concentration profiles can also be measured and used in conjunction with measured or calculated flow profiles to determine the Intrinsic Dissolution Rate, IDR in mg/min/cm$^2$. Furthermore, the optical cell assemblies described above, in combination with the fine spatial resolution of the sensor 502, allow fast analysis of poorly soluble compounds as measurement of the IDR requires only a small amount of the substance to be removed to a few hundred microns from the surface. The optical cell assemblies described above furthermore allow a variety of materials to be studied, including powders, gels and liquids. As an alternative method of determining IDR, the optical cell assembly can be weighed before and after exposure of the sample to the media. The present invention allows the real time observation of the interaction of the exposed API/formulation surface with the dissolution medium.

Figure 10:
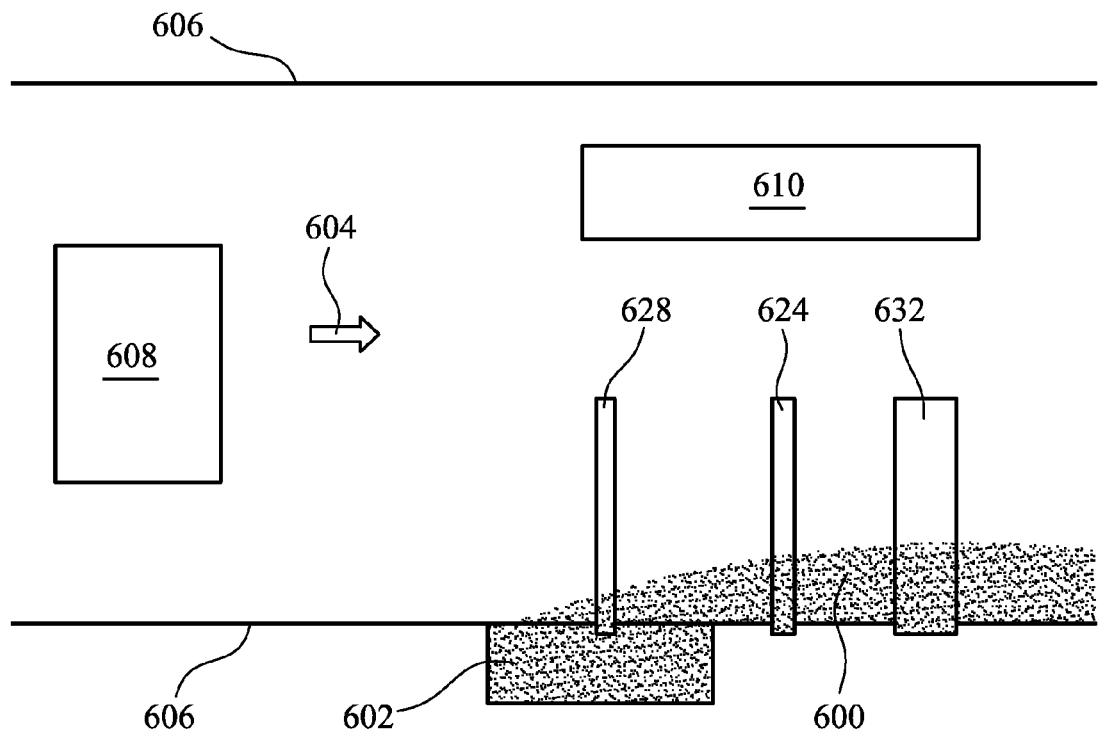
FIG. 10 is a cross sectional view of a chamber of an optical cell assembly imaged using the optical apparatus of FIG. 9.

Referring now to FIG. 10, this illustrates the an image obtained from the array detector showing a plume of analyte 600 extending from a sample 602. The sample 602 is exposed to a flowing dissolution medium, which flows in the direction indicated by arrow 604 through a chamber indicated by chamber walls 606. The image is shows the light absorbance of the analyte. Darker areas (specifically, the plume 600) correspond to areas of increased light absorbance, and hence areas of increasing concentration of the analyte within the dissolution medium. First and second reference areas 608, 610 are indicated. In order to quantify the absorbance of light due solely to the analyte within plume 600, this may be reference to the light transmitted through the dissolution medium within the chamber in the reference areas 608, 610 which do not contain any of the analyte. Reference area 608 contains no analyte because it is upstream of the sample 602. Reference area 610 contains no analyte because the plume passes swiftly downstream due to the flow of the dissolution medium before the analyte can diffuse across to the other chamber wall 606.

Figure 11:
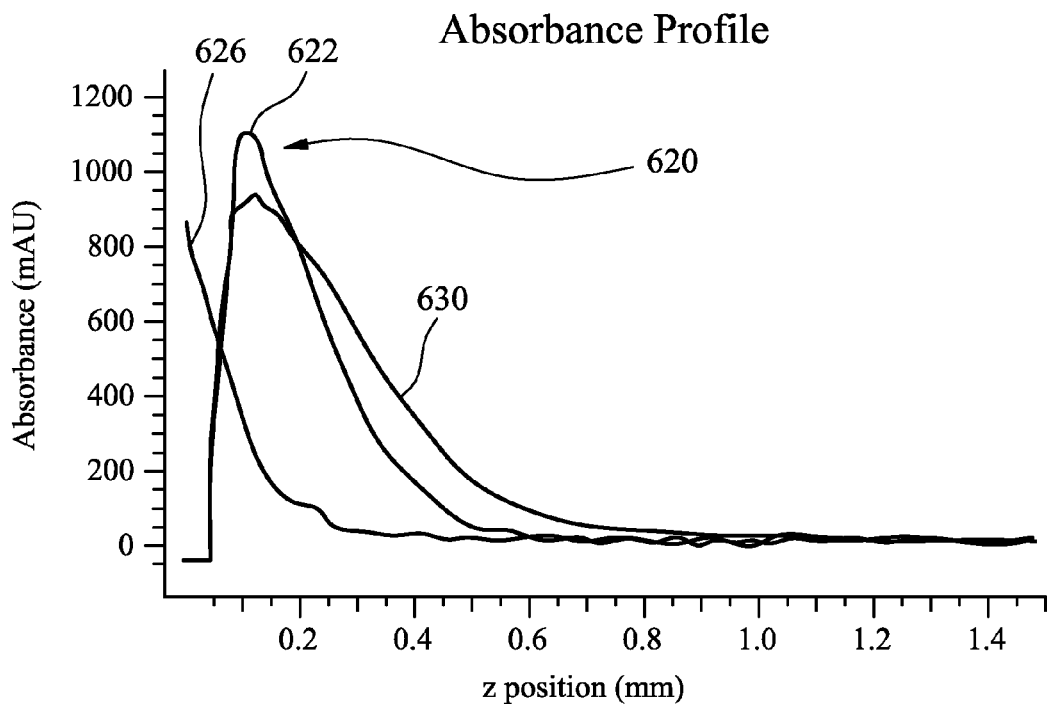
FIG. 11 is an absorbance profile corresponding to the cross sectional view of FIG. 10.

FIG. 11 illustrates absorbance profiles for selected portions of the analyte plume 600. The degree of absorbance is shown relative to Z position (extending away from the surface of sample 602 or the chamber wall 606). Arrow 620 points to absorbance profile 622, which corresponds to the absorbance due to the analyte within region 624 of FIG. 10. Absorbance profile 626 has no maximum peak and corresponds to region 628, which extends directly from the surface of the sample 602. Absorbance profile 630 corresponds to region 632 and is the furthest downstream of the sample 602. Absorbance profiles 622 and 630 have peaks which are spaced apart from the chamber wall 606, which shows that the plume does not closely follow the chamber wall. The profile used to determine the IDR is the profile which extends to the greatest X distance from the sample.

The principal advantage of the present invention is in being able to determine the concentration profiles of the active pharmaceutical ingredient (API) in space and in time close to the surface of the sample. This is not possible using other techniques for dissolution monitoring, which use ultraviolet absorbance to look at the API in the bulk solution remote from the surface. The actual concentrations and their variation with distance perpendicular to the surface are key parameters in understanding fundamentals of drug product dissolution. Previous methodologies for dissolution monitoring infer these parameters from monitoring time dependent change of concentration in the bulk solution, and using a theoretical treatment of how this time-dependent change relates to properties of the surface and the dissolution layer. Some of these theory-based inferences (e.g. that concentration at surface is equal to the solubility), are found to be questionable as seen from results using the surface imaging approach of the present invention.

A second advantage of the present invention is that only a small volume of the solution is required for measurement. The optical apparatus 500 may be the ActiPix SDI300, commercially available from Paraytec Limited. The detector examines the space within microns of the sample surface. Within this space there is no dilution of the concentration of the API. This is in contrast to prior techniques which look at the bulk solution remote from the sample, where the surface volume (microliters) is diluted to milliliters (for instance, using the Mini-IDR™ technology referred to above) or 500-900 cm$^3$ (conventional dissolution technology). Thus the present invention offers far higher sensitivity than previous methodologies, and the potential for faster analysis. This is of particular relevance to sparingly soluble APIs, and slow release formulations where analysis can be performed in less than 10 minutes—significantly faster than previously known techniques. For sparingly soluble compounds, knowing the rate at which surface dissolution happens saves time relative to waiting for the bulk concentration of the API in the medium to reach adequate, measurable levels.

Various modifications may be made to the foregoing without departing from the spirit and scope of the present invention.

The invention claimed is:

1. An optical apparatus comprising:
    a light source;
    an array detector for area imaging; and
    an optical cell assembly comprising a chamber having a generally elliptical longitudinal cross-section, the chamber being adapted to receive a sample of a material including an analyte,
    the optical cell assembly further comprising a fluid inlet and a fluid outlet coupled to the chamber and arranged to provide a fluid dissolution medium stream passing through the chamber and over the sample subsequent to receiving the sample such that the sample dissolves into the dissolution medium to form a plume extending downstream from the sample;
    wherein the optical cell assembly is positioned such that the chamber is in at least one light path created between the light source and the array detector; and
    wherein the array detector comprises a two dimensional array of detector locations arranged progressively further downstream from the sample along the chamber to provide an output signal indicative of the light absorbance of the analyte within the chamber such that the output of the array detector is indicative of a series of concentration profiles of the analyte at locations within the plume adjacent to the detector locations.

2. An apparatus according to claim 1, wherein the plurality of detector locations are arranged to provide a signal indicative of the two dimensional distribution of light absorbance of the dissolution medium and the analyte across at least part of the chamber.

3. An apparatus according to claim 1, wherein the array detector is arranged to receive light which passes through the chamber and light from the light source which does not pass though the chamber at spatially separated portions of the array detector such that light received directly from the light source may be used as a reference for light passing through the chamber.

4. An apparatus according to claim 1, wherein the array detector is arranged to receive light which passes through part of the chamber containing the dissolution medium and the analyte released into the dissolution medium and light from the light source which passes though part of the chamber containing only the dissolution medium at spatially separated portions of the array detector such that light received through only the dissolution medium may be used as a reference for light passing through the dissolution medium and the analyte.

5. An apparatus according to claim 1, wherein the light source emits at least one wavelength of light that is absorbed by the analyte comprised in the sample for detection, the absorbance of which is to be detected.

6. An apparatus according to claim 1, wherein the light source is arranged to provide UV-visible light having a wavelength in the range 180 to 1200 nm.

7. An apparatus according to claim 1, wherein the array detector comprises a solid state sensing device, preferably a CMOS APS, a CCD or a CID.

8. An apparatus as claimed in claim 1, further comprising a cartridge in which the optical cell assembly is received, the cartridge being arranged to mount the optical cell assembly relative to the light source and the array detector such that the chamber is in at least one light path created between the light source and the array detector, the cartridge comprising:
    a cartridge body having a pair of spaced, opposed arms;
    a passage extending through the arms and which passage is shaped to receive the optical cell assembly;
    wherein the arms define a space there-between, which space extends in a direction transverse to the passage, and which space is positioned such that the optical cell assembly chamber is located within the space when the optical cell assembly is located within the passage, to thereby provide at least one path for light transmitted from the light source along the space and to the chamber for testing the sample in the chamber.

9. An apparatus according to claim 1, wherein the optical cell assembly comprises:
    a hollow outer cell portion; and
    an insert portion shaped to fit within the hollow outer cell portion;
    wherein the insert portion defines a fluid flow channel extending in a direction along a length of the insert portion and which comprises the fluid inlet, the fluid outlet and the chamber disposed between the inlet and the outlet, the chamber adapted to receive the sample and having a maximum width dimension in a direction transverse to a main axis of the fluid flow channel which is greater than a corresponding width of the inlet; and
    wherein the outer cell portion and the insert portion are arranged such that, when the insert portion is fitted within the outer cell portion, light from the light source can pass through the chamber in a direction along the width dimension of the chamber.

10. An apparatus according to claim 9, wherein the chamber has a maximum cross-sectional area in a plane transverse to a plane in which the fluid flow channel is disposed greater than a corresponding cross-sectional area of the inlet, and optionally also a corresponding cross-sectional area of the outlet.

11. An apparatus according to claim 9, wherein the insert portion comprises opposed lateral windows which open on to the chamber, the windows provided on respective side surfaces of the insert portion, the windows being closed when the insert portion is fitted within the outer cell portion.

12. An apparatus according to claim 9, wherein the chamber is at least partially bound by one or more walls defined by the insert portion, which wall or walls extend between the inlet and the outlet and are shaped to define a smooth transition from the inlet towards a region of the chamber of maximum width dimension and a smooth transition from the region of the chamber of the maximum width dimension towards the outlet.

13. An apparatus according to claims 12, wherein the walls are arcuate and shaped such that the chamber is generally parabolic in longitudinal cross-section in regions adjacent to the inlet and the outlet.

14. An apparatus according to claim 9, wherein the chamber comprises a receiving area for receiving a material, and a dissolution area.

15. An apparatus according to claim 14, wherein the sample receiving area is spaced from a side wall or walls of the insert portion, so as to define a gap or gaps between the side wall or walls and the sample receiving area.

16. An apparatus according to claim 15, wherein the insert portion comprises a main insert portion element defining the dissolution area, and a sample holder element defining the sample receiving area.

17. An apparatus according to claim 16, wherein the sample receiving area is a secondary chamber defined by the sample holder element.

18. An apparatus according to claim 16, wherein the sample holder element is adapted to be received within a recess in the main insert portion element.

19. An apparatus according to claim 9, wherein the insert portion defines a charging channel for charging material into the chamber, and which charging channel is separate from the part of the fluid flow channel defining the inlet.

20. A detection method for measuring a concentration profile of an analyte near the surface of a sample, the method comprising:
   illuminating a chamber of an optical cell assembly with a light source, the chamber having a generally elliptical longitudinal cross-section and containing a sample of a material including an analyte, the optical cell assembly further comprising a fluid inlet and a fluid outlet coupled to the chamber;
   supplying a dissolution medium to the fluid inlet under pressure such that a fluid dissolution medium stream passes over the sample such that the sample dissolves into the dissolution medium to form a plume extending downstream from the sample;
   detecting light from the light source passing through the chamber at an array detector, the array detector comprising a two dimensional array of detector locations arranged progressively further downstream from the sample along the chamber; and
   generating at each detector location in the array detector a signal indicative of the light absorbance of the analyte at corresponding locations within the chamber along the light path from source to detector such that the output of the array detector is indicative of a series of concentration profiles of the analyte at locations within the plume adjacent to the detector locations.

21. A detection method according to claim 20, further comprising generating at the array detector a signal indicative of the two dimensional distribution of light absorbance of the dissolution medium and the analyte across the detection window.

22. A detection method according to claim 20, such that the output of the array detector is indicative of the concentration profile of the analyte downstream from the surface of the sample.

23. A detection method according to claim 20, such that a first output of the array detector is indicative of the flow profile of the dissolution medium downstream of the surface of the sample and a second output of the array detector is indicative of the the concentration profile of the analyte downstream of the surface of the sample, the method further comprising determining the intrinsic dissolution rate of the sample from the flow profile of the dissolution medium downstream of the sample and the concentration profile of the analyte downstream of the surface of the sample.

24. An optical apparatus comprising:
   a chamber having an opening along a sidewall of the chamber;
   a holder element adapted to introduce a sample of a material including an analyte to the chamber, the holder element being mateable with the chamber so that the sample is introducible through the opening;
   a fluid inlet and a fluid outlet coupled to the chamber and arranged to provide a fluid dissolution medium stream passing through the chamber such that the sample introduced to the chamber dissolves into the dissolution medium to form a plume extending downstream from the sample;
   a light source adapted to illuminate the chamber;
   an array detector for area imaging including an array of detector locations arranged progressively further downstream from the sample along the chamber to provide an output signal indicative of the light absorbance of the analyte within the chamber such that the output of the array detector is indicative of a series of concentration profiles of the analyte at locations within the plume adjacent to the detector locations.

* * * * *